US009615947B2

(12) United States Patent
Shinya et al.

(10) Patent No.: US 9,615,947 B2
(45) Date of Patent: Apr. 11, 2017

(54) ARTIFICIAL BLOOD VESSEL USING DECELLULARIZED BLOOD VESSEL SHEET

(71) Applicant: THE CHEMO-SERO-THERAPEUTIC RESEARCH INSTITUTE, Kumamoto (JP)

(72) Inventors: Noriko Shinya, Kumamoto (JP); Takanori Uchida, Kumamoto (JP); Akio Kishida, Tokyo (JP); Tetsuya Higami, Kobe (JP)

(73) Assignee: THE CHEMO-SERO-THERAPEUTIC RESEARCH INSTITUTE, Kumamoto (JP)

( * ) Notice: Subject to any disclaimer, the term of this patent is extended or adjusted under 35 U.S.C. 154(b) by 41 days.

(21) Appl. No.: 14/650,051

(22) PCT Filed: Dec. 17, 2013

(86) PCT No.: PCT/JP2013/083749
§ 371 (c)(1),
(2) Date: Jun. 5, 2015

(87) PCT Pub. No.: WO2014/109185
PCT Pub. Date: Jul. 17, 2014

(65) Prior Publication Data
US 2015/0313731 A1    Nov. 5, 2015

(30) Foreign Application Priority Data

Jan. 8, 2013 (JP) ................................ 2013-001033

(51) Int. Cl.
*A61F 2/06* (2013.01)
*A61F 2/82* (2013.01)
(Continued)

(52) U.S. Cl.
CPC .................. *A61F 2/82* (2013.01); *A61F 2/06* (2013.01); *A61F 2/062* (2013.01);
(Continued)

(58) Field of Classification Search
CPC ...... A61F 2/82; A61F 2230/0069; A61F 2/06; A61F 2/062; A61F 2240/002;
(Continued)

(56) References Cited

U.S. PATENT DOCUMENTS 6,187,039 B1 * 2/2001 Hiles .......................... A61F 2/06
  623/1.41
6,254,627 B1 * 7/2001 Freidberg .................. A61F 2/07
  606/195
(Continued)

FOREIGN PATENT DOCUMENTS

JP    2007-268239    10/2007
JP    2009-50297     3/2009
(Continued)

OTHER PUBLICATIONS

Office Action dated Aug. 8, 2016 in corresponding Australian patent application No. 2013373262.
(Continued)

*Primary Examiner* — Paul Prebilic
(74) *Attorney, Agent, or Firm* — Wenderoth, Lind & Ponack, L.L.P.

(57) ABSTRACT

An artificial blood vessel that can be transplanted to blood vessels with a small diameter, can be adjusted to an arbitrary size of a diameter, improves in invasiveness when a graft is taken, and overcomes the problem on the provision of a graft is provided. An artificial blood vessel prepared from a decellularized tubular structure, which is prepared by processing a decellularized, sheet-like blood vessel (decellularized blood vessel sheet) into a roll structure, and a tissue
(Continued)

adhesive, wherein a portion which is contacted with blood that flows within the artificial blood vessel consists of the tissue of the tunica intima lined with the tissue of the tunica media whereas a portion of the sheet that overlaps when the sheet is processed into a roll structure (overlap width) consists of the tissue of the tunica media and wherein a tissue adhesive is applied to the overlap width.

29 Claims, 2 Drawing Sheets

(51) Int. Cl.
- *A61L 27/36* (2006.01)
- *A61L 27/50* (2006.01)
- *A61L 27/54* (2006.01)

(52) U.S. Cl.
CPC ....... *A61L 27/3625* (2013.01); *A61L 27/3683* (2013.01); *A61L 27/507* (2013.01); *A61L 27/54* (2013.01); *A61F 2230/0069* (2013.01); *A61F 2240/002* (2013.01); *A61L 2300/252* (2013.01); *Y10T 156/1038* (2015.01)

(58) Field of Classification Search
CPC ............. A61L 27/3625; A61L 27/3683; A61L 27/507; A61L 27/54; A61L 2300/252; A61L 2209/20; A61L 2209/22; A61L 2400/18; A61L 2420/02; A61L 2420/06; A61L 2420/08; A61L 2430/20; A61L 2430/22; A61L 2430/40
USPC ............................ 623/1.44, 1.47, 1.48, 2.13
See application file for complete search history.

(56) References Cited

U.S. PATENT DOCUMENTS

| | | | |
|---|---|---|---|
| 8,883,210 B1* | 11/2014 | Truncale | C12N 5/0654 424/484 |
| 2010/0179639 A1* | 7/2010 | Bloor | A61L 27/3625 623/1.15 |
| 2011/0054588 A1* | 3/2011 | Xu | A61L 27/3604 623/1.13 |

FOREIGN PATENT DOCUMENTS

| | | |
|---|---|---|
| WO | 2009/025398 | 2/2009 |
| WO | 2014/034759 | 3/2014 |

OTHER PUBLICATIONS

First Office Action dated Mar. 24, 2016 issued in corresponding Chinese patent application No. 201380069242.X (with English translation).

International Preliminary Report on Patentability issued Jul. 23, 2015 in International Application No. PCT/JP2013/083749.

International Search Report issued Apr. 1, 2014 in International (PCT) Application No. PCT/JP2013/083749.

N. L'Heureux et al., "Tissue-Engineered Blood Vessel for Adult Arterial Revascularization", The New England Journal of Medicine, vol. 357, No. 14, pp. 1451-1453, Oct. 4, 2007.

T. N. McAllister et al., "Effectiveness of Haemodialysis Access with an Autologous Tissue-Engineered Vascular Graft: A Multicentre Cohort Study", The Lancet, vol. 373, Issue 9673, pp. 1440-1446, Apr. 25, 2009.

R. Gauvin et al., "A Novel Single-Step Self-Assembly Approach for the Fabrication of Tissue-Engineered Vascular Constructs", Tissue Engineering: Part A, vol. 16, No. 5, pp. 1737-1747, Feb. 2010.

Extended European Search Report issued Aug. 5, 2016 in corresponding European patent application No. 13871129.6.

Rie Matsushima et al., "Decellularized dermis—polymer complex provides a platform for soft-to-hard tissue interfaces", Materials for Biological Applications, 2014, vol. 35, pp. 354-362, Nov. 14, 2013.

Nam et al., "In Vivo Characterization of a Decellularized Dermis—Polymer Complex for Use in Percutaneous Devices", Artificial Organs, 2014, vol. 38, No. 12, pp. 1060-1065, Dec. 2014.

Rie Matsushima et al., "Preparation of percutaneous device by incorporating polymer with decelluarized tissue composite", the 27th Annual Meeting of the Society of Life Support Engineering (ABML2011), OS2-4, pp. OS2-4-1 to OS2-4-2, Nov. 2011.

Kimura et al., "New attempt for preventing postoperative intraperitoneal adhesion using fibrin film", Acta Obstetrica et a Gynaecologica Japonica, vol. 41, No. Supplement, pp. S-325, 450 with English abstract, Feb. 1989.

Hashimoto et al., The Journal of the Japanese Practical Surgeon Society, vol. 57, No. 12, pp. 3000-3004 with English abstract, Oct. 8, 1996.

Okazaki et al., "Study of the effect of peritoneal adhesion prevention after surgery by spraying tissue adhesive", Japanese Journal of Gynecologic and Obstetric Endoscopy, 1992, vol. 8, No. 1, p. 111 with English abstract.

* cited by examiner

ARTIFICIAL BLOOD VESSEL USING DECELLULARIZED BLOOD VESSEL SHEET

TECHNICAL FIELD

The present invention relates to an artificial blood vessel for use in graft of a blood vessel and a process for preparing the same.

BACKGROUND ART

For atherosclerosis of coronary arteries and peripheral blood vessels, therapy by surgical replacement or bypass surgery is performed. For affected parts with a diameter of 5 mm or less, an autologous blood vessel is a preferable graft for replacement wherein the most frequently used grafts are autologous internal mammary artery, radial artery and saphenous vein, which are known to have a good patency rate. However, there are problems such as unavoidable invasion for obtaining a graft, variability of its length or quality depending on each case, and unavailability of a graft in reoperation cases where a graft has already been used.

On the other hand, an artificial blood vessel such as Dacron and ePTFE has been used for revascularization of peripheral arteries of limbs but cannot be used in blood vessels with a small diameter such as coronary arteries due to early formation of thrombus and hypertrophy of the tunica intima. In recent years, it has become possible to coat the lumen of an artificial blood vessel with vascular endothelial cells by seeding the cells within the artificial blood vessel with a tissue engineering technique to thereby prevent blood coagulation. However, before surgery, the bone marrow must be taken from patients, cultivated and engrafted to an artificial blood vessel, which takes time and is costly. In particular, in cases of urgency such as coronary artery bypass, its utility is low.

DISCLOSURE OF THE INVENTION

Technical Problem to be Solved by the Invention

The problem to be solved by the present invention is to provide an artificial blood vessel that can be transplanted to blood vessels with a small diameter, can be adjusted to an arbitrary size of a diameter, improves in invasiveness when a graft is taken, and overcomes the problem on the provision of a graft.

Means for Solving the Problems

The present inventors have earnestly studied in order to solve the aforementioned problems and as a result have found that an artificial blood vessel prepared by treating a decellularized blood vessel sheet so that a portion which is contacted with blood that flows consists of the tissue of the tunica intima lined with the tissue of the tunica media whereas a portion of the sheet that overlaps when the sheet is processed into a roll structure (overlap width) consists of the tissue of the tunica media after removal of the tissue of the tunica intima, said decellularized blood vessel sheet being prepared either by processing a blood vessel from animals into a sheet followed by decellularization or by decellularizing a blood vessel from animals followed by processing the same into a sheet, and processing the decellularized blood vessel sheet into a roll structure with a tissue adhesive has an excellent pressure resistance and patency after grafting. Thereby the present invention has been completed.

Thus, the present invention may include an artificial blood vessel prepared from a decellularized tubular structure, which is prepared by processing a decellularized, sheet-like blood vessel (decellularized blood vessel sheet) into a roll structure, and a tissue adhesive, wherein a portion which is contacted with blood that flows within the artificial blood vessel consists of the tissue of the tunica intima lined with the tissue of the tunica media whereas a portion of the sheet that overlaps when the sheet is processed into a roll structure (overlap width) consists of the tissue of the tunica media and wherein a tissue adhesive is applied to the overlap width.

In addition, the present invention includes a process for preparing an artificial blood vessel comprising the steps (1) to (5) as follows:

(1) a step of preparing a decellularized blood vessel sheet of either (A) or (B):

(A) a step of processing a blood vessel from animals into a sheet to prepare a blood vessel sheet and a step of decellularizing the blood vessel sheet to prepare a decellularized blood vessel sheet, or (B) a step of decellularizing a blood vessel from animals to prepare a decellularized blood vessel and a step of processing the decellularized blood vessel into a sheet to prepare a decellularized blood vessel sheet, (2) a step of treating the decellularized blood vessel sheet so that a portion which is contacted with blood that flows within the artificial blood vessel when the sheet is processed into a roll structure consists of the tissue of the tunica intima lined with the tissue of the tunica media whereas a portion of the sheet that overlaps when the sheet is processed into a roll structure (overlap width) consists of the tissue of the tunica media with the tissue of the tunica intima being removed, (3) a step of applying a tissue adhesive to the overlap width of the decellularized blood vessel sheet, (4) a step of processing the decellularized blood vessel sheet into a roll structure and pasting the overlap width together to prepare an artificial blood vessel, and (5) a step of coating the circumferential surface of the resulting artificial blood vessel with a tissue adhesive.

Also, the present invention may include a kit for an artificial blood vessel comprising a decellularized blood vessel sheet or a decellularized tubular structure, which is prepared by processing the decellularized blood vessel sheet into a roll structure, and a tissue adhesive, wherein a portion which is contacted with blood that flows within the artificial blood vessel consists of the tissue of the tunica intima lined with the tissue of the tunica media whereas a portion of the sheet that overlaps when the sheet is processed into a roll structure (overlap width) consists of the tissue of the tunica media and wherein a tissue adhesive is applied to the overlap width.

Effects of the Invention

In accordance with the present invention, (1) it becomes possible to prepare an artificial blood vessel of a small diameter that can be transplanted to blood vessels with a small diameter; (2) it is possible to prepare a blood vessel of various diameters from the decellularized blood vessel sheet to thereby allow for preparing an artificial blood vessel fitted to blood vessels at the site of grafting; (3) in case that a blood vessel from heterologous animals is used, the problem on the provision of a graft or invasiveness into other tissues than affected parts are remedied; (4) even if a blood vessel from heterologous animals is used, the immunological rejection does not occur or is highly reduced since a scaffold is decellularized; and (5) after grafting, the lumen is covered with the endothelium and the autologous tissue is taken into the scaffold to thereby provide an artificial blood vessel which has patency for a long period of time and is ideal close to an autologous blood vessel.

BEST MODE FOR CARRYING OUT THE INVENTION

Figure 1:
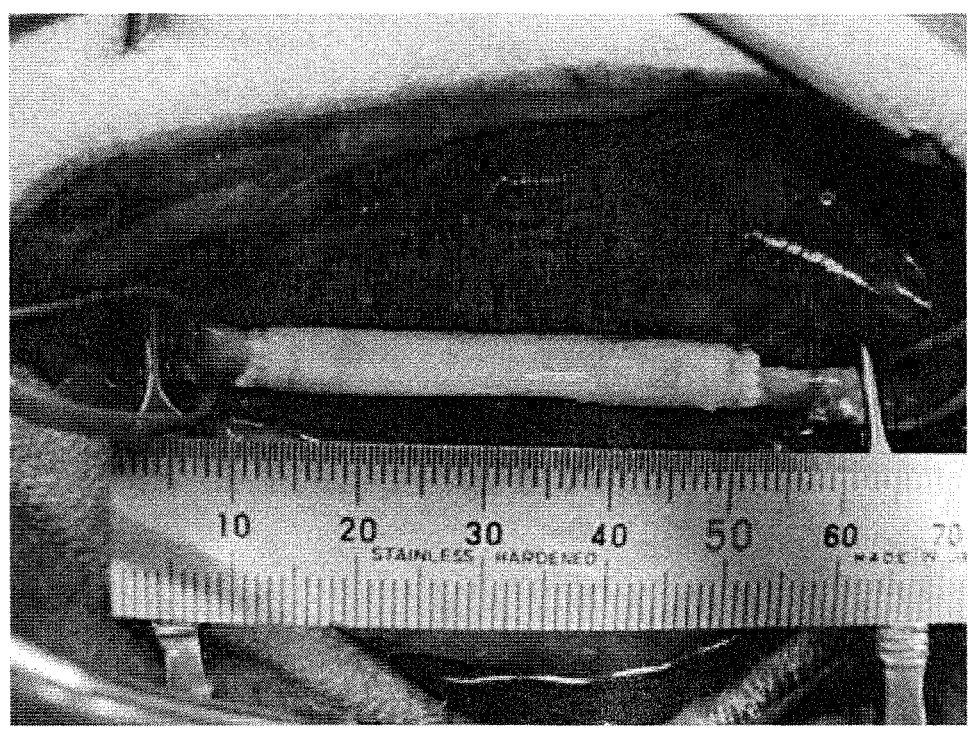
FIG. 1 is a photograph of the artificial blood vessel of the present invention when grafted.

The present invention may include an artificial blood vessel prepared from a decellularized tubular structure, which is prepared by processing a decellularized, sheet-like blood vessel (decellularized blood vessel sheet) into a roll structure, and a tissue adhesive, wherein a portion which is contacted with blood that flows within the artificial blood vessel consists of the tissue of the tunica intima lined with the tissue of the tunica media whereas a portion of the sheet that overlaps when the sheet is processed into a roll structure (overlap width) consists of the tissue of the tunica media and wherein a tissue adhesive is applied to the overlap width.

As used herein, the tissue of the tunica media is a laminar tissue rich in the elastic lamina present under the tunica intima.

As used herein, the tissue of the tunica intima is a tissue consisting of the supporting tissue (basement membrane) of endothelial cells and mainly collagen fiber.

As used herein, a tissue adhesive is used for maintaining the shape of the artificial blood vessel and includes fibrin glue, a cyanoacrylate polymerizable adhesive and gelatin glue where gelatin and resorcinol are cross-linked with formalin. The use of fibrin glue as a tissue adhesive is particularly preferable.

When fibrin glue is used as a tissue adhesive, it is preferable for improving the pressure resistance of the artificial blood vessel of the present invention that, after fibrinogen is rubbed to an overlap width, thrombin and fibrinogen are applied.

The artificial blood vessel of the present invention may preferably be such that, when fibrin glue is used as a tissue adhesive, thrombin is applied at 1 U/mL to 160 U/mL.

The artificial blood vessel of the present invention may preferably be such that, when fibrin glue is used as a tissue adhesive, fibrinogen is applied at 4 mg/mL to 250 mg/mL.

The artificial blood vessel of the present invention may be prepared such that its size of an inner diameter may suitably be selected depending on a size of blood vessels at the grafting site. For instance, the artificial blood vessel with an inner diameter of about 1 mm to about 20 mm is selected.

The decellularized blood vessel sheet of the present invention may preferably be the one prepared by processing a blood vessel from animals into a sheet followed by decellularization or the one prepared by decellularizing a blood vessel from animals followed by processing into a sheet.

As used herein, blood vessels are preferably selected from arteries or veins. In particular, arteries may preferably be selected from the group consisting of the aorta, the carotid, the internal mammary artery, the radial artery and the gastro-epiploic artery.

The artificial blood vessel of the present invention may be such that a tissue adhesive is coated on its circumferential surface since the artificial blood vessel exerts the effect of improved pressure resistance and reduced tissue adhesion when the circumferential surface of the artificial blood vessel is coated with a tissue adhesive.

The pressure resistance of the artificial blood vessel of the present invention may suitably be altered depending on the grafting site and preferably is 400 mmHg or more.

The present invention includes a process for preparing an artificial blood vessel comprising the steps (1) to (5) as follows:

(1) a step of preparing a decellularized blood vessel sheet of either (A) or (B):

(A) a step of processing a blood vessel from animals into a sheet to prepare a blood vessel sheet and a step of decellularizing the blood vessel sheet to prepare a decellularized blood vessel sheet, or (B) a step of decellularizing a blood vessel from animals to prepare a decellularized blood vessel and a step of processing the decellularized blood vessel into a sheet to prepare a decellularized blood vessel sheet, (2) a step of treating the decellularized blood vessel sheet so that a portion which is contacted with blood that flows within the artificial blood vessel when the sheet is processed into a roll structure consists of the tissue of the tunica intima lined with the tissue of the tunica media whereas a portion of the sheet that overlaps when the sheet is processed into a roll structure (overlap width) consists of the tissue of the tunica media with the tissue of the tunica intima being removed, (3) a step of applying a tissue adhesive to the overlap width of the decellularized blood vessel sheet, (4) a step of processing the decellularized blood vessel sheet into a roll structure and pasting the overlap width together to prepare an artificial blood vessel, and (5) a step of coating the circumferential surface of the resulting artificial blood vessel with a tissue adhesive.

When fibrin glue is used as a tissue adhesive, the process for preparing the artificial blood vessel of the present invention preferably includes in step (3) a step of rubbing fibrinogen to an overlap width and a step of applying thrombin and fibrinogen to the overlap width.

The process for preparing the artificial blood vessel of the present invention may be such that the decellularization is selected from the group consisting of high hydrostatic pressure, a surfactant, an enzyme, hypertonic solution/hypotonic solution, and freeze-thawing.

The process for preparing the artificial blood vessel of the present invention may be such that the decellularization is the one where the structure of the basement membrane is maintained after decellularization.

The process for preparing the artificial blood vessel of the present invention may preferably further include a step of treating with DNase and/or a step of treating with an alcohol.

The present invention may include a kit for an artificial blood vessel comprising a decellularized blood vessel sheet or a decellularized tubular structure, which is prepared by processing the decellularized blood vessel sheet into a roll structure, and a tissue adhesive, wherein a portion which is contacted with blood that flows within the artificial blood vessel consists of the tissue of the tunica intima lined with the tissue of the tunica media whereas a portion of the sheet that overlaps when the sheet is processed into a roll structure (overlap width) consists of the tissue of the tunica media and wherein a tissue adhesive is applied to the overlap width.

The present invention is further explained in more detail by means of the following Examples but is not limited thereto.

Example 1

Preparation of Artificial Blood Vessel with Small Diameter with BOLHEAL and Decellularized Artery Sheet and Pressure Resistance Test (1) Test Method The swine aorta was made into a sheet. The tunica adventitia was peeled off overall and the tunica intima was peeled off in a range of ½ to ⅔. The sheet was treated under a high hydrostatic pressure and washed with a DNase solution for 7 days, with an alcohol for 3 days, and with a citrate buffer for 3 days. Water was wiped off from the surface of the decellularized swine aorta sheet as prepared. To the surface where the tunica intima was peeled off (the surface where the tunica media tissue was exposed), a fibrinogen solution (BOLHEAL) was rubbed and after 3 minutes a mixture of the fibrinogen solution and a 10-fold diluted thrombin solution (BOLHEAL) was applied. Using this surface as an overlap width, the sheet was crimped for 5 minutes into a roll structure wherein only the tunica intima tissue was exposed on the surface of the lumen of the artificial blood vessel the outside of which was covered with the tunica media tissue to form a double structure. The lumen was washed with a saline. To the circumference of the artificial blood vessel were sprayed a fibrinogen solution and a thrombin solution. The artificial blood vessel was immersed in a saline supplemented with 100 unit/mL of heparin sodium and was subject to sterilization under a high pressure. One end of the artificial blood vessel as prepared was clamped with a forceps and the other end was inserted with a cannula and ligated. To the cannula were connected a syringe and a manometer. A saline in the syringe was introduced into the lumen of the artificial blood vessel and a pressure at which the artificial blood vessel was ruptured was measured as pressure resistance.

(2) Results; Pressure Resistance

Pressure resistance of 375±61.2 mmHg was obtained (n=4).

Example 2

Graft Test in Goat of Artificial Blood Vessel with Small Diameter with BOLHEAL and Decellularized Artery Sheet (1) Test Method The right carotid of goat was exposed and partly removed under anesthesia and replaced with the artificial blood vessel prepared as in Example 1 (inner diameter: about 4 mm, length: about 5 cm) by anastomosis. To the anastomosed part was rubbed a fibrinogen solution and then were sprayed a fibrinogen solution and a thrombin solution. While treatment, a 5% glucose solution supplemented with heparin sodium was administered via instillation. Three minutes before clamping the carotid, 300 unit/kg of heparin sodium was administered intravenously in a single dose. No postoperative anticoagulant treatment was done. Three weeks after the treatment, the animal was subject to euthanasia and the treated part was sampled for pathological examination.

(2) Results

Autopsy: All the artificial blood vessels were in patency. The lumen showed a smooth surface with no sign of thrombus, obstruction or aneurysmal dilatation.

Figure 2:
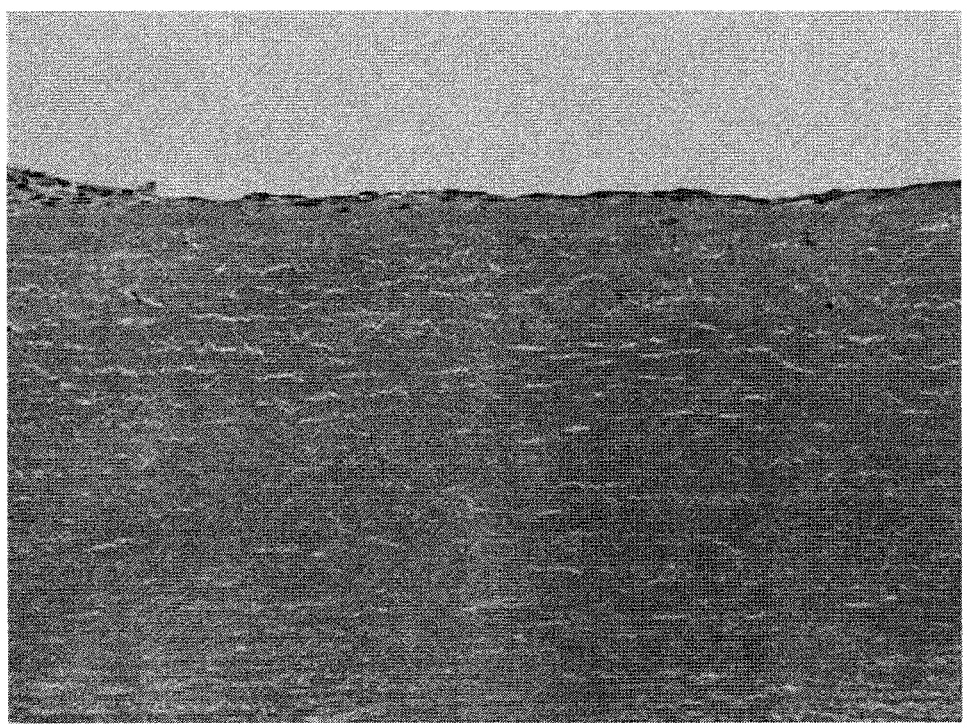
FIG. 2 is a photograph of the tissue of the vascular wall of the artificial blood vessel of the present invention three weeks after grafting.

Pathological tissue examination: A layer of endothelial cells was observed in the lumen of the artificial blood vessel (FIG. 2). The autologous tissue penetrated the vascular wall of the artificial blood vessel accompanied by capillary angiogenesis therein to form an autologous blood vessel-like structure.

INDUSTRIAL APPLICABILITY

The artificial blood vessel of the present invention can be used e.g. for the manufacture of material of medical application.

The invention claimed is:

1. An artificial blood vessel prepared from a decellularized tubular structure, which is prepared by processing a decellularized blood vessel sheet into a roll structure, and a tissue adhesive, wherein a portion which is configured to be contacted with blood that flows within the artificial blood vessel comprises a tunica intima lined with a tunica media, wherein an overlap width portion of the sheet that overlaps when the sheet is processed into the roll structure consists of the tunica media, and wherein the tissue adhesive is applied to the overlap width portion.

2. The artificial blood vessel according to claim 1 wherein the tissue adhesive is fibrin glue.

3. The artificial blood vessel according to claim 2 wherein fibrinogen is rubbed to the overlap width portion and thereafter, thrombin and fibrinogen are applied to the overlap width portion.

4. The artificial blood vessel according to claim 1 wherein an inner diameter of the artificial blood vessel is about 1 mm to about 20 mm.

5. The artificial blood vessel according to claim 1 wherein the decellularized blood vessel sheet is prepared by processing a blood vessel from animals into a sheet followed by decellularization or, is prepared by decellularizing a blood vessel from animals followed by processing into a sheet.

6. The artificial blood vessel according to claim 1 wherein a blood vessel from which the decellularized blood vessel sheet is prepared is selected from arteries or veins.

7. The artificial blood vessel according to claim 6 wherein the blood vessel from which the decellularized blood vessel sheet is prepared is selected from the group consisting of the aorta, the carotid, the internal mammary artery, the radial artery and the gastro-epiploic artery.

8. The artificial blood vessel according to claim 1 wherein the tissue adhesive is coated on a circumferential surface of the artificial blood vessel.

9. The artificial blood vessel according to claim 1 wherein a pressure resistance is 400 mmHg or more.

10. A process for preparing an artificial blood vessel comprising the steps (1) to (5) as follows:
(1) a step of preparing a decellularized blood vessel sheet by either (A) or (B):
(A) a step of processing a blood vessel from animals into a sheet to prepare a blood vessel sheet and a step of decellularizing the blood vessel sheet to prepare the decellularized blood vessel sheet, or
(B) a step of decellularizing a blood vessel from animals to prepare a decellularized blood vessel and a step of processing the decellularized blood vessel into a sheet to prepare the decellularized blood vessel sheet, (2) a step of treating the decellularized blood vessel sheet so that a portion which is configured to be contacted with blood that flows within the artificial blood vessel when the sheet is processed into a roll structure consists of a tunica intima lined with a tunica media, wherein an overlap width portion of the sheet that overlaps when the sheet is processed into the roll structure comprises the tunica media with the tunica intima being removed, (3) a step of applying a tissue adhesive to the overlap width portion of the decellularized blood vessel sheet, (4) a step of processing the decellularized blood vessel sheet into the roll structure and pasting the overlap width portion together to prepare an artificial blood vessel, and (5) a step of coating a circumferential surface of the artificial blood vessel with the tissue adhesive.

11. The process according to claim 10 wherein the tissue adhesive is fibrin glue.

12. The process according to claim 11 wherein step (3) further includes a step of rubbing fibrinogen to the overlap width portion and a step of applying thrombin and fibrinogen to the overlap width portion.

13. The process according to claim 10 wherein an inner diameter of the artificial blood vessel is about 1 mm to about 20 mm.

14. The process according to claim 10 wherein the blood vessel from which the decellularized blood vessel sheet is prepared is selected from arteries or veins.

15. The process according to claim 14 wherein the blood vessel from which the decellularized blood vessel sheet is prepared is selected from the group consisting of the aorta, the carotid, the internal mammary artery, the radial artery and the gastro-epiploic artery.

16. The process according to claim 10 wherein the decellularization is carried out by high hydrostatic pressure, a surfactant, an enzyme, hypertonic solution/hypotonic solution, or freeze-thawing.

17. The process according to claim 10 wherein the structure of a basement membrane is maintained after decellularization.

18. The process according to claim 10 which further includes a step of treating with DNase and/or a step of treating with an alcohol.

19. The process according to claim 10 wherein a pressure resistance is 400 mmHg or more.

20. A kit for an artificial blood vessel comprising the artificial blood vessel as set forth in claim 1 and a tissue adhesive.

21. The kit according to claim 20 wherein the tissue adhesive is fibrin glue.

22. The kit according to claim 21 wherein fibrinogen is rubbed to the overlap width portion and thereafter, thrombin and fibrinogen are applied to the overlap width portion.

23. The kit according to claim 20 wherein an inner diameter of the artificial blood vessel is about 1 mm to about 20 mm.

24. The kit according to claim 20 wherein the decellularized blood vessel sheet is prepared by processing a blood vessel from animals into a sheet followed by decellularization or, is prepared by decellularizing a blood vessel from animals followed by processing into a sheet.

25. The kit according to claim 20 wherein a blood vessel from which the decellularized blood vessel sheet is prepared is selected from arteries or veins.

26. The kit according to claim 25 wherein the blood vessel from which the decellularized blood vessel sheet is prepared is selected from the group consisting of the aorta, the carotid, the internal mammary artery, the radial artery and the gastro-epiploic artery.

27. The kit according to claim 20 wherein the tissue adhesive is coated on a circumferential surface of the artificial blood vessel.

28. The kit according to claim 20 wherein a pressure resistance is 400 mmHg or more.

29. A kit for an artificial blood vessel comprising a decellularized blood vessel sheet and a tissue adhesive, wherein the decellularized blood vessel sheet comprises:
 a tunica intima;
 a tunica media; and
 an overlap width portion consisting of the tunica media which is exposed and configured to be contacted with the decellularized blood vessel sheet when the sheet is processed into a roll structure.

\* \* \* \* \*